United States Patent [19]
Lee

[11] 4,027,662
[45] June 7, 1977

[54] AUTOMATIC BLOOD PRESSURE RECORDER

[75] Inventor: Arnold S. J. Lee, Englewood, N.J.

[73] Assignee: Milstein Medical Research Foundation, Inc., New York, N.Y.

[22] Filed: Sept. 26, 1975

[21] Appl. No.: 617,175

Related U.S. Application Data

[63] Continuation of Ser. No. 378,167, July 11, 1973, abandoned.

[52] U.S. Cl. .................. 128/2.05 A; 128/2.05 Z; 128/2.05 Q
[51] Int. Cl.[2] ........................................ A61B 5/02
[58] Field of Search ....... 128/2.05, 2.05 A, 2.05 G, 128/2.05 M, 2.05 Z, 2.05 Q; 346/33 ME

[56] References Cited

UNITED STATES PATENTS

| | | | |
|---|---|---|---|
| 2,447,018 | 8/1948 | Keinath | 128/2.05 Q |
| 2,821,188 | 1/1958 | Pigeon | 128/2.05 A |
| 2,827,040 | 3/1958 | Gilford | 128/2.05 A |
| 3,101,082 | 8/1963 | Steen et al. | 128/2.05 M |
| 3,146,777 | 9/1964 | Lee | 128/2.05 A |
| 3,236,230 | 2/1966 | Follett | 128/2.05 A |
| 3,504,663 | 4/1970 | Edwards | 128/2.05 G |
| 3,533,401 | 10/1970 | Streu | 128/2.05 A |
| 3,636,941 | 1/1972 | Guevrekian | 128/2.05 A |
| 3,773,033 | 11/1973 | Rodbard et al. | 128/2.05 M |
| 3,779,235 | 12/1973 | Murphy, Jr. et al. | 128/2.05 M |
| 3,814,083 | 6/1974 | Fletcher | 128/2.05 A |

OTHER PUBLICATIONS

*Southwestern Inst. of Elect. & Electronic Engng. Conf. Record*, Apr., 1968, pp. 17F1–17F5.

Primary Examiner—Kyle L. Howell

[57] ABSTRACT

A pneumatic regulator including a constant-volume reference chamber and associated pressure-sensitive inflation and deflation valves is provided to effect a precise linear depressurization of an inflatable cuff which has been applied to a patient and pressurized to a value higher than the patient's systolic pressure. Pulses obtained from an ultrasonic or other suitable detector sensitive to movements of the patient's arterial wall in synchronism with the blood flow surges as the cuff is depressurized below the patient's systolic pressure are integrated and then translated into variable-duration marking impulses. Such impulses are successively applied to the actuating input of a pen or other marker associated with an X-Y recording chart, the pen being linearly scanned along one chart axis at the constant depressurization rate of the cuff. During such scan, the pen records, on the chart, a linear pattern of marks each of which has a length corresponding to the duration of the marking impulse then applied to its actuating input. Facilities are also described for operating an alarm when the patient's systolic or diastolic pressure does not fall within a prescribed range and for accurately and rapidly distinguishing valid blood flow surges from artifacts during the cuff depressurization.

27 Claims, 11 Drawing Figures

AUTOMATIC BLOOD PRESSURE RECORDER

This is a continuation of application Ser. No. 378,167, filed July 11, 1973 now abandoned.

This invention relates to improvement in automatic blood pressure measurement machines, and is particularly concerned with an automatically operating machine for taking a plurality of blood pressure measurements and graphically recording the measurements in such form that a trained observer can readily determine changes in the condition of the patient as well as readily distinguishing valid pressure measurements from artifacts in each such measurement.

BACKGROUND OF THE INVENTION

In the past a number of inventors have sought to provide machines that automatically detect blood pressure and automatically indicate and/or record the detected measurements in such manner that a physician or other trained observer can rapidly determine the systolic and diastolic pressures at a glance from the recording and can easily distinguish the valid pressure markings from artifacts. The prior art has also sought to provide machines that periodically take a series of such measurements at spaced time intervals inan automatic manner and record such measurements in a comparatively disposed arrangement such that the observer can quickly determine changes in the condition of the patient from the different measurements. Such continuing record data is particularly desirable for use in hospital operating rooms and in intensive care units at hospitals.

In an earlier patent of the present inventor, U.S. Pat. No. 3,146,777 a machine of this general type is provided in which each blood pressure measurement is graphically recorded as a series of single valued spaced dashes along a line; and with a plurality of such time spaced measurements being recorded in substantially parallel lines disposed transversely along a moving record. This recording enables a physcan to very rapidly distinguish changes in the condition of the patient.

SUMMARY OF THE INVENTON

According to the present invention there is provided a moe comprehensive and versatile machine that provides the above described functions, and many others, in either a completely automatic or in a semi-automatic fashion. Additionally the machine provides various improvements in the detection and in the recording of the blood pressure measurements such that artifactual recordings are more readily distinguishable at a glance from valid blood pressure representing recordings.

Very geneally according to the invention, blood pressure is indirectly measured by detecting the effects of the blood flow surges which occur whenever the flow starts up in an artery which has been compressed to flow cutoff, as an external pressurize applying cuff is depressurized over the range of pressures ranging from systolic to below diastolic pressure. The detected signals are electronically processed to derive modulated electrical pulse signals representative of the "strength" of the blood flow surges. The modulated electrical pulses are then recorded in a graphical manner as either single values functions, or alternativly with other measurements as multi-valued functions to provide additional information; all to enable a valid and rapid indication of systolic and diastolic pressure, and to clearly distinguish valid pressure signals from artifacts.

A number of alternative manners of recording or marking the data on a record are disclosed for enabling other physiological measurements to be recorded or to enable a blood pressure function to be recorded with greater resolution.

In an alternative embodiment, an "off-line" mode is shown that functions to automatically determine the probable existance of artifacts in any measurement, and upon such determination, to automatic recycle the machine as soon as possible to repeat the measurement. In this mode, the machine may be present or adjustably programmable to provide a given number of repeating cycles in the event of determining recurring error and thereupon to provide a suitable alarm in the event of failure to provide a valid measurement.

In such an "off-line" mode, the machine may be provided with means for automatically adjusting the gain of the recording mechanism to provide a desired graphic reproduction of the signals; and/or in the event of determining excessive noise in the detected signal, to automatically adjust the gain of the detector and recycle the machine for a new measurement.

In still further embodiments, the machine may be provided with means for automatically determining when either the detected systolic or diastolid pressures do not fall within given ranges and to automatically trigger an alarm under such circumstances to alert the physician or nurse to a condition of danger.

The most comprehensive and versatile machine according to the present invention might incorporate all of the above noted automatic features and improvements. Alternatively, one or more of the various features may be provided in a less sophisticated machine to operate automatically, or in a semi-automatic manner, as might be desired for particular applications.

DESCRIPTION OF A PREFERRED EMBODIMENT

Very generally according to one embodiment of the invention, an adjustable automatic timer periodically initiates the rapid inflation and relatively slow deflation of a flexible cuff encircling the arm of a patient over the range of pressures exceeding systolic to below diastolc pressure, and during each deflation portion of the cycle a series of blood flow surges are detected to generate electrical signals in response to each opening of the artery from a collapsed condition. As is well known, the arterial system of the body and surrounding tissue are substantially elastic and the external pressure cuff serves to collapse the artery whenever external pressure in the cuff exceeds internal arterial pressure, and alternatively, the artery walls decollapse or open when the internal pressure exceeds the external, resulting in a blood flow surge. The series of electrical signals are electrically processed to minimize artifacts and the processed signals are then applied to modulate a pen or suitable marker in such fashion as to graphically record a single valued function, with the individual markings on the record providing an adjustable indication of the strength of the blood flow surges and the position of such markings across the record indicating both the externally applied pressure in the cuff at the time of the surge and the time of the surge during the deflation cycle. As in Applicant's earlier patent referred to above, the plural markings for each measurement are recorded along a line transversely across a slowly moving record. Along the length of the record in the direction of its movement the record is printed with the time of day to show the time at which each measurement is made. The record is also printed in a direction transverse to its direction of movement according to pressure graduations so that the location of the markings show the cuff pressure. The record is preferably continuously driven during the automatic operation of the machine so that for each succeeding measurement, the record has been advanced to enable the series of processed signals corresponding to surges to be recorded in a line disposed in parallel relationship to the line of markings for the preceeding measurement. Since for each measurement, each marking along the line corresponds to a different cuff pressure, the first marking for each measurement indicates the systolic pressure and the last marking indicates diastolic pressure.

Figure 1:
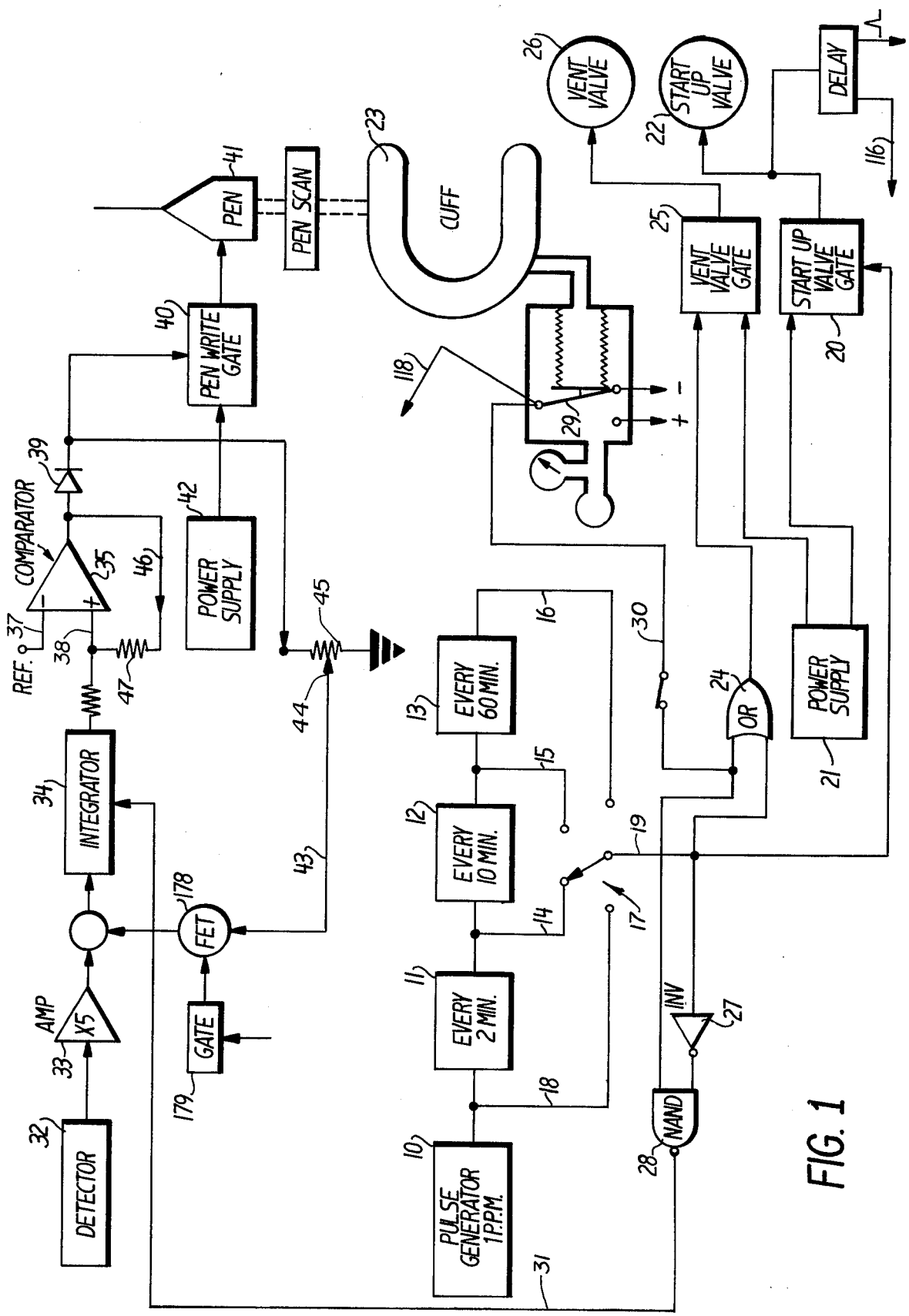
FIG. 1 is an electrical schematic diagram illustrating a preferred embodiment for recording only a single valued function.

With this general introduction, reference is now made to FIG. 1, showing an electrical system for a preferred embodiment.

As shown, an automatic timer mechanism comprises an electronic oscillator 10 producing uniform pulses of four second duration and at a slow frequency of one such pulse every minute. These oscillator pulses are directed to three frequency dividers 11, 12, 13 disposed in cascaded relationship providing successive frequency division of scale of two, scale of 5, and scale of 6, respectively. Accordingly, the output of 14 of divider 11 produces one such pulse every two minutes; divider 12 produces an output pulse over line 15 every ten minutes; and divider 13 produces an output pulse over line 16 every sixty minutes. A manually adjustable multiposition switch 17 is provided with terminals connected to all output lines 18, 14, 15, and 16, and accordingly the switch 17 is adjustable to select repetition of the machine every minute, every two minutes, every ten minutes, or every sixty minutes, as might be desired.

These timer generated pulses are directed over line 19 to initiate operation of both the pneumatic system for inflating the cuff, and the detecting and recording system for recording the measurements.

For initiating the pneumatic cuff inflation mechanism, the timer pulse from selector switch 17 is directed over line 19 to a start-up valve gate 20, thereby opening the gate 20 to energize a solenoid operated start-up valve 22 which is powered by a power supply 21. The start-up valve 22 is thereby opened for the four second interval of the timer pulse to apply air pressure from a pressurized source to inflate the cuff 23. Concurrently, the timer pulse over line 19 is also passed through "or" circuit 24 to energize a vent valve gate 25, thereby closing a normally open solenoid vent valve 26. As will be seen, this prevents venting of the pressurising system during inflation of the cuff 23.

The timer pulse over line 19 is also directed to an inverter circuit 27 and to a "Nand" circuit 28 to ready or condition the electrical detecting and measuring system for operation.

As the cuff 23 is inflated to beyond a preset "dump" pressure, a bellows operated switch 29 responsive to cuff pressure is closed to apply a voltage of the correct polarity over line 30 to the second input of Nand circuit 28, whereby the Nand circuit is thereupon properly energized to produce a reset pulse over 31 to the integrator in the electrical system for conditioning the electrical system to commence a new operation.

The signal over line 30 from bellows switch 29 is also passed through "or" circuit 24 to the vent valve gate 25, thereby maintaining the solenoid operated vent valve 26 in a closed condition and preventing venting of the pneumatic system during this portion of the cycle of blood pressure measurement.

Upon the cuff 23 being inflated to a preset pressure above systolic during the four second interval, it immediately commences to depressurise in a precisely controlled linear manner, as will be described; and during such linear depressurization portion of the cycle, a suitable detector 32 detects a series of blood flow surges that occur as the cuff pressure is progressively diminished between systolic and diastolic pressure.

For example, the cuff pressure is initially rapidly inflated to some present pressure over systolic, such as above 150 Torr, and the cuff is then depressurized in a linear manner at a rate of about 6 Torr every second to a dump pressure below distolic; over a time interval of about 30 seconds. As the cuff pressure diminishes toward the patient's systolic pressure, the arteries are periodically collapsed and then opened following each heart beat, thereby producing a blood flow surge during each opening, and such surges are detected by detector 32 to produce an electrical burst signal for each such surge.

In a preferred embodiment, the detector employed is of the doppler ultrasonic type, such as is disclosed in Ware U.S. Pat. No. 3,527,197, that produces an electrical burst signal proportional to the rate-of-movement of the arterial wall. However, it will be appreciated by those skilled in the art that other detectors, incuding microphones, may be employed for this purpose to detect the surges as disclosed in Applicant's earlier application.

These low level blood flow surge signal bursts are amplified by a factor of about 5 by an amplifier 33, and then rectified; and the rectified and amplified negative polarity bursts are then suitably processed by an "interposition" circuit to minimize the transmission of artifacts and meaningfully energize the recorder. As will be seen, the purpose of the interposition circuit is to assist in minimizing the recording of spurious signals and to obtain quantized pulses for recording that are representative of the strength of the blood flow surges. Since the preferred doppler type ultrasonic detector 32 produces burst signals proportional to the rate-of-movement of the arterial wall, a preferred interposition circuit operates to integrate these bursts, and to provide pulses of variable duration in proportion to the "size" of the bursts, including their amplitude and duration. It will be understood, however, by those skilled in the art that these bursts may be processed according to other mathematical functions to derive useful signals for recording that will indicate to the physician the strength of the blood flow surge through the artery.

Returning to FIG. 1, each of the amplified and rectified burst signals is applied as a negative polarity signal to an integrator 34 to rapidly raise th output of integrator 34 to dc level according to the combined amplitude and duration of its input, and to retain the output at this dc level. This characterized by producing either a negative or positive dc output at constant amplitude of about 12 volts depending upon the values of the combination of input voltages on its dual inputs 37 and 38. The output of comparator 35 is normally at negative voltage due to a reference voltage applied at input 37; and a diode 39 in the output circuit prevents the further transmission of this constant negative voltage. However, upon the output of integrator 34 rising above a present level, the output of the comparator 35 is promptly "jumped" to its positive voltage level which is transmitted through diode 39 to energize the pen gate circuit 40 controlling the marking by the pen 41 or other recording marker that is powered by power supply 42. So long as the output of comparator 35 is positive, the pen 41 or marker is continuously energized by its power supply 42 to provide a continuous marking.

However, as will be recalled in this embodiment it is desired to graphically rcord dashes of adjustable length proportional to the strength of the detected surges. This is performed by feeding back a low level constant positive dc voltage from the output of comparator 35 over line 43 to the input of integrator 34 in opposition to the original negative voltage from the detector circuit. This constant dc feedback is obtained via a potentiometer 44 and a series resistor 45 that are coupled to the output of diode 39. As previously noted, the voltage over line 43 is positive and in opposition to the negative going detector signals, and is also at a much lower level than such signals whereby this constant feedback signals is progressively integrated by integrator 34 and operates to slowly lower or diminish the output of integrator 34 from the output level that it reached when driven by the previously received negative signal from the detector circuit. After a period of time related to the level of the previously integrated detector signals, the output of integrator 34 is progressively diminished to below the level of the reference voltage applied to comparator 35, and the comparator output is accordingly flipped backwardly or returned from its constant positive voltage output to its original constant negative level. This negative output is not transmitted through diode 39, and the energizing signal applied to the pen gate 40 controlling the marking by pen 41 is accordingly terminated, thereby to terminate the marking by the pen 41 in response to that detected blood pressure surge. In short, the integrator 34 provides a variable amplitude output correspondingly to the detected surge signal and the combination of integrator and comparator convert this to a pulse of adjustable width or time duration.

Briefly recapitulating the functioning of the detector circuit and interposition circuit, each blood flow surge occurring when the cuff pressure is between systolic and diastolic pressure is detected by the ultrasonic doppler detector 32 to produce a low level signal burst characterized by representing the rate-of-movement of the artery during movement from a collapsed to an open condition. This low level burst signal is amplified to a useful level and rectified, and then applied to a store and hold integrator 34, having a variable output amplitude corresponding to the content of the detector burst. This jump in integrator output drives the output of a comparator 35 from a constant negative voltage to a constant positive voltage, thereby energizing the pen 41 to commence writing. A constant low level positive signal is also directed backwardly to the integrator to progressively diminish the output of integrator 34 from the level of the "stored" detector burst, and thereby after a variable time duration that is proportional to the amplitude of the integrated burst signal, the comparator 35 is flipped backwardly to its constant negative voltage to terminate the marking or recording by the pen 41.

To prevent a spurious artifact signal from inadvertantly triggering the operation of the comparator 35, the comparator circit is provided with positive feedback from its output to input, via line 46 and summing resistor 47. The effect of this feedback is to require a greater positive polarity signal than the reference signal on line 37, to initially trigger the comparator 35 to jump from its negative to positive output and start the writing of the pen; and conversely to require that the integrator output be driven below the reference voltage on line 37 in order to terminate the writing of the pen. This is performed as follows: before writing of the pen 41, the output of comparator 35 is at contant negative polarity, and a small portion of this negative signal is fed back to the input over feedback 46. To trigger the comparator 35, the output of integrator 34 must then exceed the sum of the reference voltage on line 37 and the level of dc feedback over line 46. Conversely, after the comparator 35 has been triggered and its output is at positive polarity, the dc feedback is in a direction or polarity opposing that of the reference on line 37, thereby diminishing the net reference voltage applied to the comparator 35. Consequently the output of integrator 34 must then be diminished to a level below the difference between reference voltage and feedback on 46 in order to trigger the comparator 35 backwardly to its initial negative output condition.

PNEUMATIC SYSTEM

According to a preferred embodiment, it is desired that during each measurement, the depressurizing or bleed of air from the cuff be regulated in a precisely linear fashion and that the scanning or positioning of the pen or marker across the record be controlled by the existing pressure in the cuff. In this manner during each measurement the recording marker is scanned across the record in a precisely linear fashion and the beginning location of each of the markings on the record corresponds to the time during the cycle when that blood flow surge is detected and also corresponds to the cuff pressure for that surge. As will be seen, this linear depressurization enables artifactual signals to be more readily distinguished from valid blood flow surges and also enables the recording to more readily indicate arrythmias in the hearbeat.

Since the inflatable cuff 23 is an elastic member whose volume changes with the degree of deflation, in order to obtain a linear or uniform decline in pressure in the cuff over the deflation portion of the cycle, it is necessary that the air be evacuated from the cuff in a nonlinear manner. According to the present invention, this controlled nonlinear bleed in the cuff is obtained by employing a constant volume reference container having rigid walls, and by linearly pressurizing and depressurizing the reference container with air to in turn regulate the linear pressurizing and depressuring of the flexible cuff. Since the reference container has a constant volume it may be precisely linearly depressurized by a constant flow evacuation of air therefrom.

Figure 2:
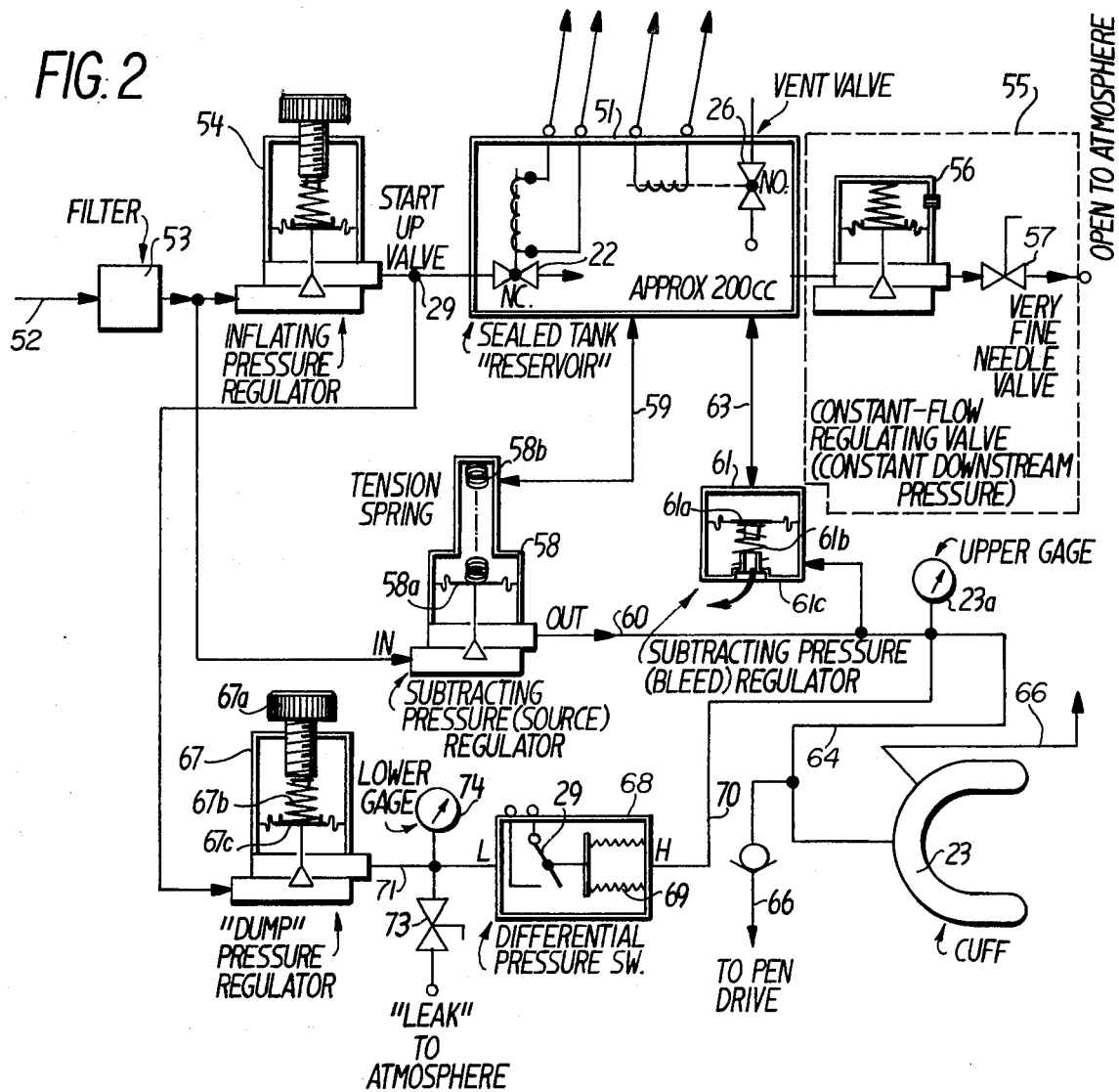
FIG. 2 is a schematic illustration depicting a preferred pneumatic system for providing a regulated linear depressurization of the cuff.

Referring to FIG. 2, for a detailed consideration of a preferred linearizing pneumatic system, a constant volume reference tank 51 is provided with a normally closed solenoid operated start-up valve 22 at the inlet 24 and a normally open solenoid operated vent valve 26 at an outlet. Upon the start-up pulse from the timer energizing the start-up valve gate 20 and energizing the vent valve gate 25, as described above, pressurized gas from a source (not shown) is directed over an inlet line 52 and through a suitable filter 53 to an adjustable inflating pressure regulator valve 54. During a short portion of the four second interval when the start-up valve 22 is closed in response to the timer pulse, the reference tank 51 is pressurized by the inlet gas to a pressure that is preset by the inflating pressure regulator valve 54, whereupon the regulator valve 54 automatically closes. This regulator valve 54 is preset to a pressure that is 5 PSI above the desired maximum pressure desired in the cuff 23.

At the outlet of the constant volume reference tank 51 is provided a constant flow regulating valve mechanism 55 that provides a regulated constant flow fo gas and accordingly a linear depressurization of air from the tank 51. This constant flow mechanism comprises a pressure regulating valve 56 disposed in series with a very fine needle valve 57 whose outlet is open to the atmosphere. The regulating valve 56 is adjusted to regulate the gas pressure at the inlet of the needle valve 57 to a constant pressure of about 5 PSI above atmospheric pressure. Therefore with a constant pressure across the needle valve 57, the needle valve passes or bleeds constant flow of air from the reference tank 51 to the atmosphere. Since the reference tank 51 encompasses fixed volume enclosure, this constant flow of air from the tank provides a regulated linear decline in pressure in the tank 51.

For pressurizing and depressurizing the flexible cuff 23, the pressurized inlet source after the inlet filter 53, is also directed to a subtracting pressure regulator valve 58 for regulating the pressure to the cuff 23 from the source. Valve 58 is of the differentially operated type having two chambers separated by a flexible diaphram 58a for operating the valve. The upper chamber is coupled to and senses the reference pressure in the tank 51 over line 59 and the lower chamber is coupled to and senses the pressure in the cuff over line 60. A tension spring 58b provides an upward pull on the diaphram 58a of about 5 PSI to maintain this valve normally closed. Upon pressurizing the tank 51, the cuff 23 is therefore rapidly inflated to a pressure of 5 PSI less than the pressure in the tank 51 through the action of the subtracting pressure regulator valve 58 that is opened to admit pressurized gas into the cuff 23 whenever the cuff pressure is more than 5 PSI less than that of the refernce tank 51. For depressuring the cuff 23 whenever its pressure is greater than within the 5 PSI of the referece tank 51, a second subtracting pressure regulator valve 61 is employed to compare and regulate the pressure in the cuff 23 to that in the reference tank 51. This second subtracting regulator valve 61 senses the pressure in the reference tank 51 via line 63, and that in the cuff 23 over line 64, and functions to bleed the cuff pressure to atmosphere whenever its outlet 61c rises to greater than 5 PSI of the pressure in reference tank 51. As generally shown, this valve 61 is also divided into upper and lower chambers by a flexible diaphram 61a, and is biased by a spring 61b. Any excess of pressure in the cuff 23 over that in the tank 51 as modified by spring operates on the diaphram to open the valve 61 and bleed the air from the cuff 23 to atmosphere until the preset differential pressure is reached, whereupon valve 61 is again closed to stop the leakage of air from the cuff 23. Thus subtracting regulator valve 58 constantly regulates the admission of pressurized gas into the cuff 23 whenever the reference tank 51 pressure is above that preset for the cuff 23, and the second subtracting regulator valve 61 exhaust compressed air from the cuff 23 to atmosphere whenever the opposite condition prevails; the combination of these two valves 58 and 61 therefore constantly regulates the pressure in the cuff 23 both upwardly and downwardly to closely follow that of the reference tank 51.

As will be recalled, the pressure in the reference tank 51 is progressively reduced at a precisely linear regulated rate by the action of the constant flow regulating valve mechanism 55. Consequently the pressure in the cuff 23 is likewise lessened at a precisely linear regulated rate by the action of the two subtracting regulating valves 58 and 61. Thus for each blood pressure measurement, the tank 51 is automatically inflated to 5 PSI above a desired pressure for the cuff and is progressively deflated or depressurized at a precisely controlled linear rate by the reference tank 51 and valve mechanism as described. As will be seen, the regulated pressure in the cuff 23 is also directed over line 66 to control the scanning movement of the pen 41 or marker so tht during the depressurization portion of the measurement cycle when the blood flow surges are being detected, the pen 41 or marker is also scanning across the record at a precisely controlled linear rate.

After the cuff has completed its linear rate of depressurization to a pressure below diastolic pressure, it is desired that the cuff pressure then be rapidly emptied or "dumped" to atmospheric pressure. The reason for this action is to promptly remove any external pressure from the limb after the measurement has completed so as not to interfere with the blood return circulation through the veins which occurs at a much lower pressure than diastolic pressure in the arteries. To perform this function, there is provided an adjustable dump pressure regulator valve 67 and a differential pressure operated switch 68. The dump pressure regulator valve 67 is similar to the adjustable inflating regulator valve 54 and is provided with a manually turnable screw 67a for adjusting the compression of bias spring 67b that operates on a diaphram 67c for opening and closing the valve mechanism. This regulator valve 67 senses and regulates a fixed preset pressure reference on line 71 leading to an inlet of differential pressure switch 68.

The other inlet to differential pressure switch 68 is over line 70 from the cuff pressure leading to an expandable bellows 69 inside the switch housing 68. So long as the pressure in the cuff 23 is above the low dump reference pressure on line 71 (preset by regulator valve 67) the bellows 68 is expanded to a position keeping electrical contacts 29 closed. As described in FIG. 1, these contacts apply energization through gate 25 to the solenoid of the vent valve 26 located at an outlet from the reference tank 51, and this energized solenoid valve 26 is kept closed to prevent venting of the reference tank 51. However, upon the cuff pressure dropping below diastolic to the preset dump level on line 71, the bellows 69 is compressed to open the electrical contacts 29 and deenergize the vent valve gate 25. Since the vent valve 26 is a normally open valve, the deenergization of its solenoid results in opening of this valve to evacuate or dump the remaining pressure in the reference tank 51 to the atmosphere. The subtracting pressure regulator valve 61 correspondingly senses the drop to atmospheric pressure of tank 51 and correspondingly vents the cuff 23 to its atmosphere. For proper functioning of the dump regulator valve 67, a very small needle valve leak 73 to atmosphere is provided in line 71 and a pressure gage 74 is provided in this line to indicate the preset level of the dump pressure.

ALARMS

Although a trained observer can usually determine with reasonable accuracy from the recording those true values of systolic and diastolic pressure from the artifacts, and can alert an attending physician to the need for prompt care when these blood pressures change to a dangerous range, a sufficient number of nurses or other observers are not continually available for this purpose. It is accordingly desired that the machine be automated to provide an alarm whenever a blood pressure measurement reveals that either the systolic pressure does not fall within a "safe" range of pressure or the diastolic pressure does not fall within a safe range of pressure.

According to the present invention, an alarm system for determining when systolic pressure does not fall within a proper range of pressures is effectively performed by measuring the time interval after the start of deflation of the cuff when the first blood surge signal is detected. Since the cuff is originally inflated to a known pressure that exceeds the systolic pressure, and since the cuff is depressurized at a precisely controlled linear rate, a given time interval or time range after deflation begins can be preset to represent a "normal" range of systolic pressures, and any measured pressure either above or below this range can be classified as abnormal and trigger the generation of an alarm.

Figure 4:
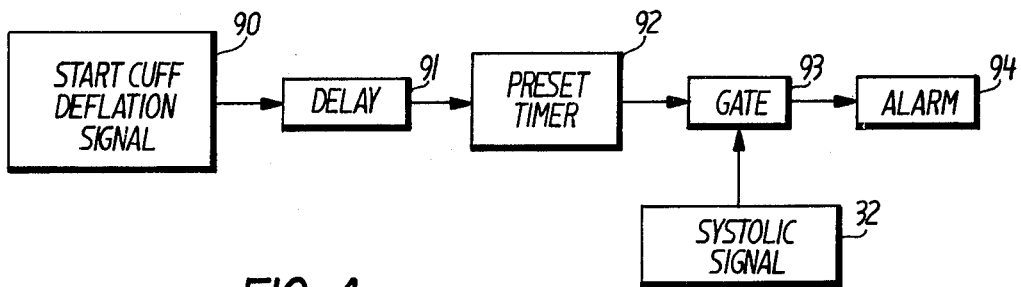
FIGS. 4 and 5 are schematic illustrations showing automatic alarm circuits employed in the system.

FIG. 4 illustrates a preferred circuit for performing this function. As shown, an electrical trigger pulse is initially produced at the beginning of cuff deflation from circuit 90 and applied to a time delay circuit 91 that delays the transmission of this pulse for a given time interval until the cuff pressure has diminished to the beginning of a suitable pressure range for systolic. The time delayed pulse then energizes a preset interval timer 92, for producing an extended inhibit pulse to a gate circuit 93, rendering the gate circuit open or nontransmissive for the fixed interval of the timer, but transmissive at any time before or after this interval. The detector system 32 is connected to an alarm 94 through this gate 93, whereby opening of the gate prevents the energization of the alarm 94 in response to detection of systolic pressure by the detector 32 when the gate is open, and conversely enables the alarm to be activated if the detection of systolic pressure is made either before or after the timer interval when the gate is normally closed. In the absence of artifact, the first detected blood surge burst during the deflation of the cuff is normally produced when the cuff pressure first declines to the systolic pressure. To minimize the possibility of a spurious triggering of the alarm, the signals from the detector 32 are suitably filtered to pass only those above a given amplitude to the gate 93.

Figure 5:
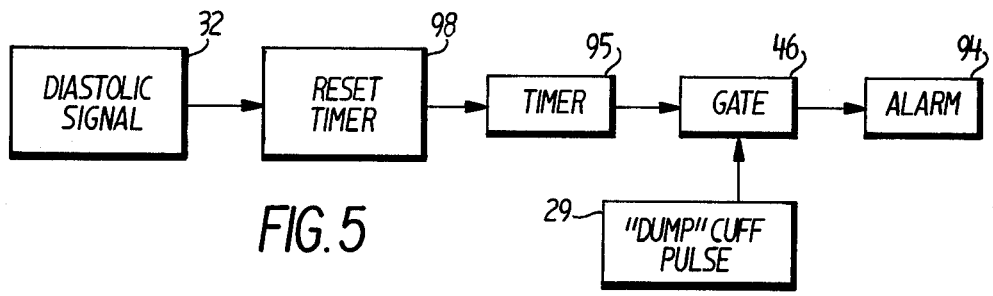

To activate an alarm in the event that the measured diastolic pressure does not fall within a proper range of such pressures, a similar alarm circuit is employed, as shown in FIG. 5. In FIG. 5, a gate circuit 96 for regulating energization of the alarm 94 is disabled by operation of a timer 95 during a preset fixed time interval or pressure range as in FIG. 4. However, in this case, the timer 95 is actuated in response to a signal obtained from the diastolic measurement 97. During the time interval produced by the timer 95, corresponding to a given normal range of diastolic pressures, the gate 96 is opened to prevent energization of the alarm 94 but before such time interval or after such interval, the gate 96 is closed for enabling the energization of the alarm. The occurance of the dump cuff pressure from differential pressure switch 29 produces a signal energizating the gate 96. This dump pressure occurs at a varible time after the detection of diastolic pressure, but occurs at a fixed preset pressure as described above in FIG. 2. Consequently if the time interval between measurement of diastolic pressure and dump cuff pressure is either too long or too short, and accordingly does not fall within the preset time range set by timer 95, the gate 96 is closed at the time of receiving a pulse from switch 29 and accordingly this gate energizes the alarm 94.

As will be recalled, in the absence of artifactual signals, the last burst signal in the series obtained from the ultrasonic detector occurs at the external cuff pressure corresponding to diastolic pressure. To insure that only the last signal of said series is employed to control the timer 95, a resettable timer 98 is connected in cascade between the diastolic signal generator 97 and the timer 95. Resettable timer 98 is of the type that is characterized by being automatically reset by each input signal and not producing an output pulse unless a fixed time interval has elasped before the last input pulse is received. In this manner each of the detected blood surge burst signals is repetitively applied to the timer 98 to repetitive-Y reset this timer until the last burst of the series is received. Only this last signal occuring at the diastolic pressure operates the timer for its full interval and therefore enables it to energize the second timer 95.

RECORDING

Figure 8:
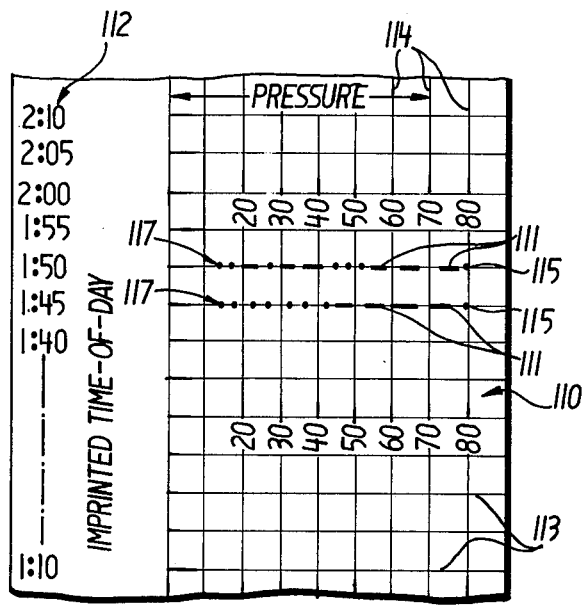
FIG. 8 shows a portion of the recording paper or web having time-of-day and pressure imprintings and typical recorded measurement.

In the embodiment of FIG. 1, a single pen or marker 41 is scanned across a record at a linear rate proportional to the linear decline in pressure in the cuff 23, and this marker is energized by pulses that are adjustably modulated in time length to record dashes of adjustable length along a line according to each such pulse. This mode of recording is depicted in FIG. 8 wherein the moving record is designated by 110, and the adjustable length dashes by 111 disposed across a line 113 for each measurement.

The continuously fed record 110 is delineated with spaced transverse lines that bears imprinting along such lines according to the time-of-day. The spacing apart of the time-of-day markings lines is in correspondence with the slow speed of moving the record so that each line of the dash recording or marking 112 is spaced from the previous line by a distance corresponding to the time-of-day between the recordings. The record is also delineated with spaced apart lines 114 running in the direction of its movement and these later delineations are imprinted with the different cuff pressures, starting at the left of the record with the highest pressure of about 300 Torr and ranging to the lowest pressure at the right. At the left of the record, for each line of recordings the pen or marker 41 is energized to place a dot 115 at the position on the record indicating the highest pressure to which the cuff is inflated. This signal applied to the marker is obtained from the output of the startup valve gate 30 over line 116 when its solenoid is deenergized, thereby signaling the commencement of deflation of the cuff 23. Since the pen or marker 41 is linearly positioned or scanned from left to right across the record 110 is proportion to the cuff pressure, the position of the pen 41 at the time of commencing deflation is at maximum cuff pressure.

In a similar manner at the far right of each line of markings is provided a dot 117 which is located on the record at a position signifying the dump pressure when the cuff is evacuated to the atmosphere on the completion of each measurement. This signal is obtained from the closing of differential pressure switch 29, and this occurs at the lowest pressure in the cuff before dumping. Thus each line of markings 112 representing a single blood pressure measurement shows on the record, the time-of-day when such measurement was made; the highest pressure and lowest pressure in the external cuff; the systolic and diastolic pressures; and a series of variable length dash markings representative of the intensity of the blood flow surges that occur during deflation of the cuff over the range of systolic to diastolic pressure. The spacing between the beginnings of each adjacent pair of such dashes are proportional to the period between successive surges since the pen or marker 41 is scanning across the record at a precisely linear rate. Consequently any irregularity between the equal spacing of the dashes is indicative of either an irregularity in the heart best or the fact that one or more of the dashes does not represent a valid blood surge signal but instead results from a spurious signal.

Figure 6:
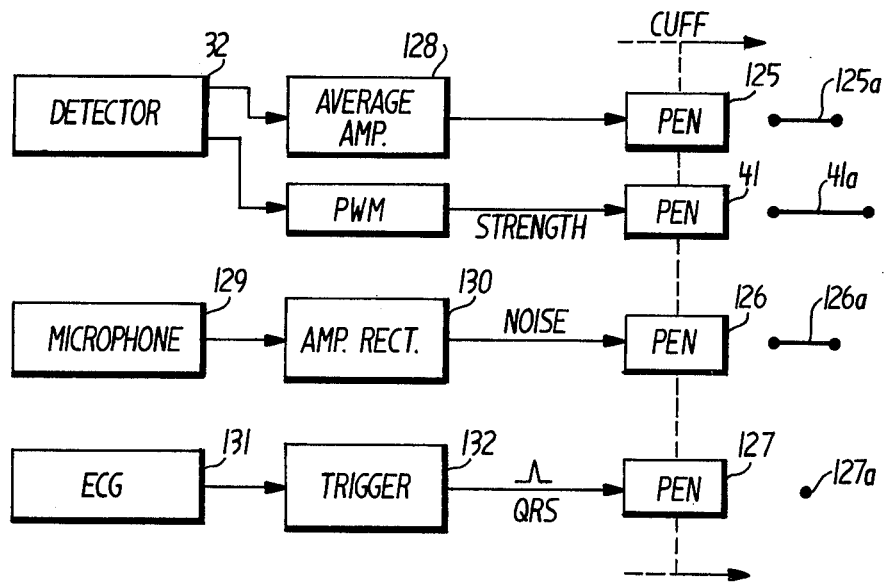
FIG. 6 is a schematic illustration showing an additional embodiment employng multiple making devices.

For recording still additional information that will enable a physician or other trained observer to distinguish valid recorded signals from artifacts, the present invention contemplates the addition of multiple pens or markings elements as shown in FIG. 6.

Referring to FIG. 6, there is shown a system employing four pens or markers 125, 41, 126 and 127 disposed in vertical alignment over the record 110 with all four pens or markers being adapted to being driven linearly in synchronism across the record in response to the lnearly decreasing pressure in the cuff. These four pens will therefore produce four parallel lines of markings across the record for each blood pressure measurement.

The upper pen or marker 125 is adapted to be energized and to record markings proportional to the average amplitude of the blood surge signals, and to provide such markings as adjustable length dashes 125a. This is performed by applying the detected and integrated surge signals from the detector 32 and interposition circuit to an averaging circuit 128.

The second pen or marker 41 independently records variable length dashes according the the strength of the detected surge signls as explained above in FIG. 1.

The third pen or marker 126 is independantly energized to provide variable length markings 126a according to the ambient noise level, resulting from ambient noise is other than the artery being detected. Such noise may be detected by a suitable placed microphone 129 for "listening" to the noise and applying the detected noise signals to an amplifier and rectifier 130 to suitable process the signals for application to the pen 126.

A still further pen or marker 127 is independantly energized by the detected ECG wave to produce a dot markings 127a at the time of each detected wave. A suitable electrode type detector and amplifier 131 may be employed to sense the ECG signals and to initiate a trigger circuit 132 for energizing the pen 127. All of these additional recordings provide further information for each measurement to enable an observer to visually distinguish from the markings of pen 41 those valid surge signals from artifacts. For example, a valid blood surge signal recorded by pen 41 will be in phase or synchronism with an ECG signals recorded by pen 127 and showing the time of a heart beat whereas recorded artifact will not be. Similarly where a large noise is detected and recorded by pen 126 at the same time as a long dash by pen 41, it will be apparent that this marking by pen 41 does not represent a valid surge but instead results from a spurious noise signal. Similarly, the average amplitude signal recorded as variable length dashes by pen 125 clearly reveals any marked anomaly since the average amplitude of the different blood surge singals will not vary over too great a range. Thus these additional recordings from pens 125, 126, and 127 all assist in revealing artifacts and in permitting an observer to quickly distinguish the valid blood surge recordings from the spurious markings. It will be apparent to those skilled in the art that either a fewer or greater number of pens may be employed as desired for recording these and other types of additional interpretive data.

Figure 7:
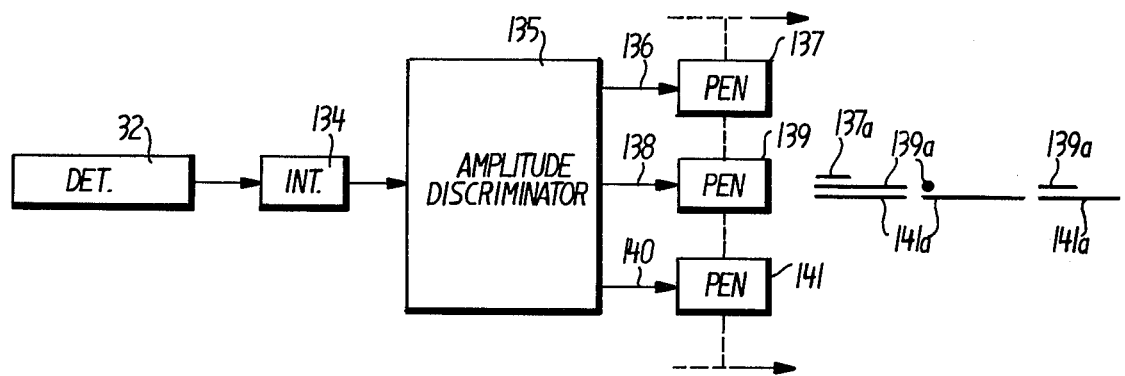
FIG. 7 is a schematic illustration showing an alternative embodiment employing multiple marking elements for improved resolution.

A plurality of pens or markers may also be employed in concerted arrangement to improve the observable resolution of the recording or markings as shown in FIG. 7.

Referring to FIG. 7, three pens or markers 137, 139, and 141 are disposed in vertical alignment over the record and are adapted to be driven or scanned across the record in syncronism and at a precisely controlled linear rate in accordance with the pressure in the cuff as previously described.

For energizing the pens in accordance with the blood surge signals, the signal from detector 32 and amplifier feeds an integrator 134 to provide at its output a signal of variable amplitude in proportion to the strength of the detected blood "surge" signals. An amplitude discriminator circuit 135 responds to the variable input signal to produce on only its lower output line 140 an output signal when such input signal is between an first and second level; and to produce an output signal on both output lines 140 and 138 when the input signal is between the second and a third higher level; and to produce an output signal on all three lines 140, 138, and 136 when the input signal is between the third and a fourth higher level. In this manner, the observable resolution of the system is improved by a factor of three by employing three pens 137, 139, and 141 to each record a portion of the variable blood surge signal, and the combination of the three to record a combined dash length over a range that is three times as long as with only one pen. Furthermore, the width of the record and the number of surges that may be recorded during each measurement remain the same as before since the plural markings for recording ech surge, such as 141a, 139a, 137a are disposed in vertical relationship one above the other in a direction of feed of the record rather than transversely across the record.

Figure 10:
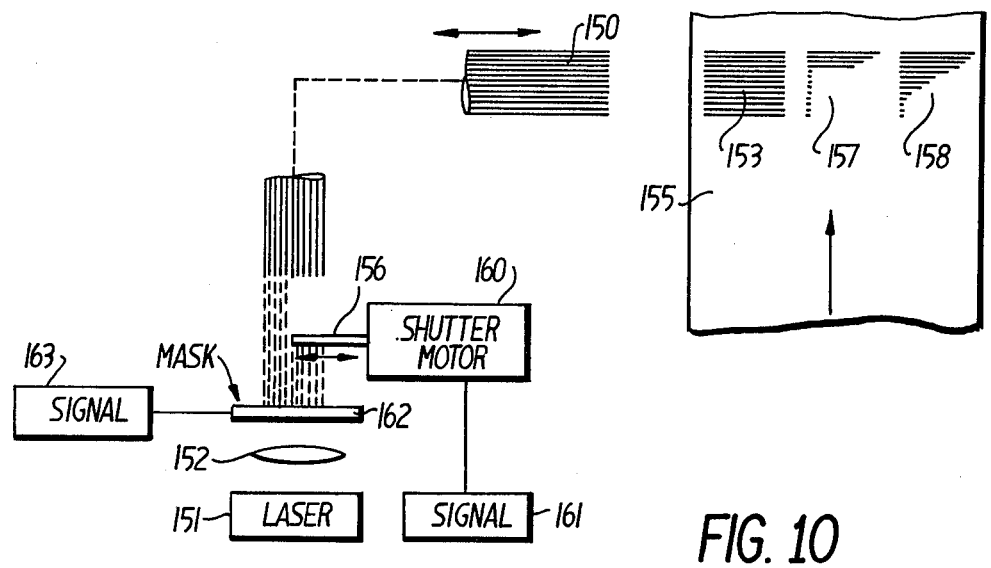
FIG. 10 is an illustration of an alternative recording device for recording multi-valued functions.

In the above described embodiments, each of the pens or markers is adapted to provide one or more markings of variable length (eg. dashes) across the record as the pen is linearly scanned across the record in a line sweep. These markings represent single valued functions of the signals applied to energize the pens. As shown in FIG. 10, a suitably configured marking element may be employed to provide a single valued function wherein each of the markings is of variable width in the direction of feed instead of variable length transverse to the direction of feed. Also as shown by FIG. 10, such a marker may be employed to record a multi-valued function by marking both a variable length and independently marking a variable width on the record.

Referring to FIG. 10, the writing or marking element in this embodiment may comprise a bundle of fine optical fibres 150 that are sufficiently flexible to permit scanning the outer end thereof across the record 110 in the same manner as previously described, according to the linearly changing pressure in the cuff 23. The remote stationary end of the fibre bundle 150 receives high intensity coherant light from a laser 151 that is appropriately focused by a lens 152. When all fibres in the bundle 150 are energized by the light, a marking or recording of finite width is produced on a light sensitive record 155 as generally illustrated by the representative marking 153. However to modulate or change the width of the marking, a transversely movable shutter 156 is positioned between the focusing lens 152 and the stationary ends of the fibre bundle to mask all or any selected portion of the fibres from the focused light source and therefore permit recording from only selected ones of the fibres. In this manner, markings of adjustable width may be made as depicted by 157 and 158. For providing signal controlled modulation of the width or thickness of the markings, a shutter motor 160 is employed to adjustably position the shutter 156 in response to a controlling signal received from 161.

To provide multi-valued markings that are independantly adjustable in both length and in width, an additional shutter 162 or mask 162 may be employed to regulate on and off the light passing to the entire bundle of fibres according to an additional signal 163. Since the free end of the fibre optical pen 150 is transversely scanning across the record 155, the mask 162 is employed to regulate the length of the marking to the direction of scanning by cutting off all light, and the adjustable shutter 156 independantly regulates the width of the marking by adjustable cutting off the light from only certain ones of the fibres. Thus employing a writing element of this kind, permits the processed blood pressure surge signal to be recorded along one dimension of the record and an additional signal such a noise, or ECG, or average amplitude, to be recorded along a different dimension. Since fibre optical bundles are readily available in very small sizes, a plurality of such writing elements may be employed in a manner illustrated in FIG. 6 to provide simultaneously recordings of twice as many functions as shown in FIG. 6.

OFF — LINE PROCESSING

To distinguish between artifacts and valid blood pressure measurements, there is provided an off-line system temporarily storing the series of detected surge signals obtained during each measurement and "testing" such signals to determine their validity or genuineness. In the event that these tests indicate the validity of the stored signals, they are repoduced from the memory bank into the recording channel of FIG. 1 and then recorded on the chart or web as previously described. If, on the other hand, the signals are found to contain probable unacceptable artifacts, then the machine is instructed to promptly recycle and repeat the blood pressure measurement and to again temporarily store the detected signals in the memory for testing again. Should the second test prove to be more valid, within the range desired, the signals are reproduced from the memory and recorded. However should the second measurement also prove to be unacceptable, the machine is again instructed to recycle and repeat its measurement. In a preferred embodiment, the machine is preprogrammed to promptly repeat its measurements up to three times at prompt intervals, such as 10 second intervals, in the event of recurring error, and after such three measurements to actuate an alarm for summoning a physician or other attendant.

Figure 3:
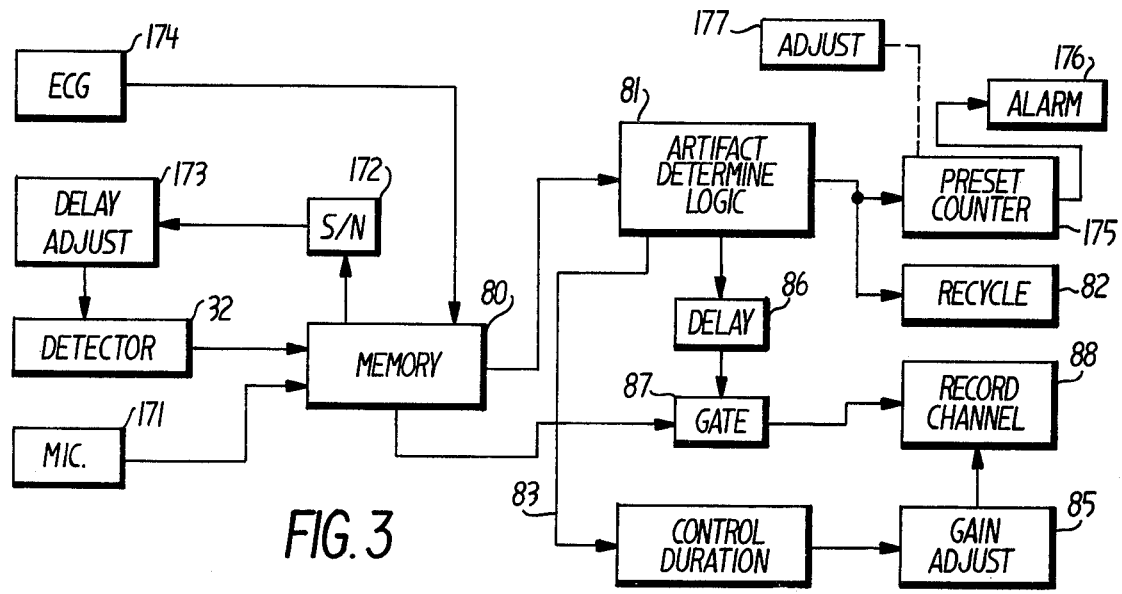
FIG. 3 is a schematic illustration of a off-line system for automatic recycling of the measurement in the event of error.

FIG. 3 is a block diagram illustrating this modification of the invention together with additional features. As shown the output of the detector 32 after suitable amplification is stored in a memory 80, such as a magnetic tape, and a series of tests of the signals are conducted by the artifact determining circuit 81. If the event of determining error, a recycle initiating circuit 82 is energized to automatically initiate a repeat measurement by the timer mechanism 170 after a ten second interval. Alternatively in the event that the tests reveal that the stored signals are within the ranges of genuineness, then two operation are performed. In the first operation; the signals are suitable processed by control circuit 84 to determine the pulse of maximum duration in that measurement and this measured quantity is employed by 85 to automatically adjust the gain of the recording channel 88.

As will be recalled from FIG. 1, the pen 41 or marking device is energized by pulses of adjustable duration to provide a marking of adjustable length across the record in proportion to the integral of each detected blood flow surge. This type of recording provides a line of broken dashes of different length across the record indicating the strength of each of the surges when the cuff is bled from systolic to below diastolic pressure. If the gain of the pulse width modulator circuit to too low, the individual recorded dashes are too long and overlap the next succeeding dash marking producing a continuous marking line across the record of across a portion thereof. Alternatively if the recorded gain is set too high, the individual surge markings are all to short, and are mainly "dot" markings that fail to reveal the desired information.

After the gain has been adjusted, a time delayed trigger produced by delay circuit 86 choses a gate 87 enabling playback of the measurement signals from the memory 80 into the recording channel 88.

A still further refinement of the system enables the gain of the ultrasonic or other detector 32 to be atuomatically adjusted in the event that the signal to noise ratio is too low. This is preferably performed by employing a microphone 171 or other detector to determine noise level and applying this determination along with the detected surge signal to determine the signal to noise ratio in 172. In the event that this ratio is too low, an adjustment is applied to circuit 173 for adjusting the gain of the detector circuit 32 prior to the next blood pressure measurement. If will be appreciated that the automatic gain adjustment will be conducted in the event that the machine in being recycled to take a new measurement since the adjustment of the detector 32 will not affect any signals previously stored in the memory 80.

Returning to FIG. 3, each instruction to the machine to automatically recycle is counted by a preset counter 175, which is preset or adjusted at 177 to count or sum a fixed number of cycles, such as 3 cycles. In the event that the machine is instruced to repetitively recycle or repeat its measurement three time, or at any other preset number, the counter 175 operates an alarm 176 to summon a physician or other attendant.

Figure 9:
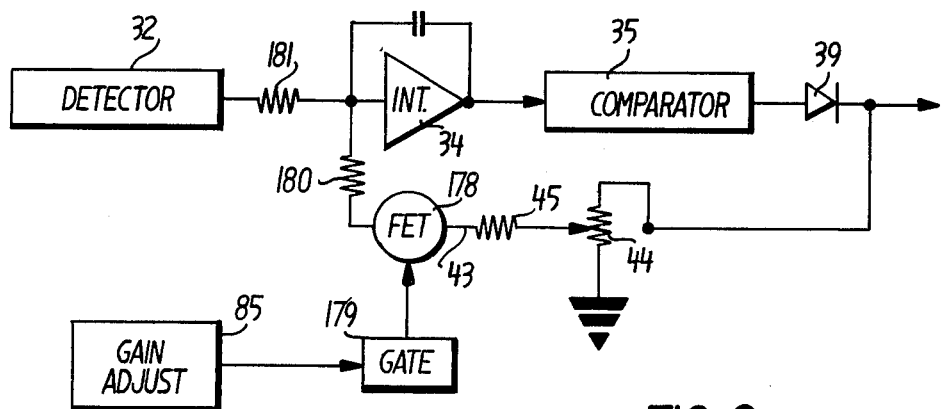
FIG. 9 is a more detailed circuit illustration showing automatic gain adjustment in the recording channel.

FIG. 9 illustrates one manner automatically adjusting the gain of the recording channel before playback from the memory to the recording mechanism. As will be recalled from FIG. 1, the detected surge signals are first amplified and rectified and then integrated by integrator 34. The variable amplitude output of integrator 34 energized a comparator circuit 35 that effectively converts the variable amplitude signals into pulses of adjustable time duration for energizing the pen or marker element to produce dashes of adjustable length. The proportionality constant relating the duration or width of the pulses to the amplitude of the integrated signals is determined by the adjustment of potentiometer 44 applying a constant positive voltage backwardly to the integrator 34. For automatically adjusting this gain or proportionality constant, the pulse of maximum width is determined from the memory (FIG. 3) by circuit 84 and applied to the gain adjusting circuit 85. At the proper time before playback of the signals form memory for recording, a gate 179 is closed, permitting the gain adjustment signal 85 to adjustably energize a field effect transistor 178, or other suitable amplitude adjustment circuit, that regulates the amplitude of the dc voltage over line 43 backwardly to the summing resistor 180 leading to the integrator 34. This automatically regulates the maximum length of the recorded dashes to less than that necessary to provide a continuous line of recording, using the maximum time duration of the recorded pulse as a reference.

Figure 11:
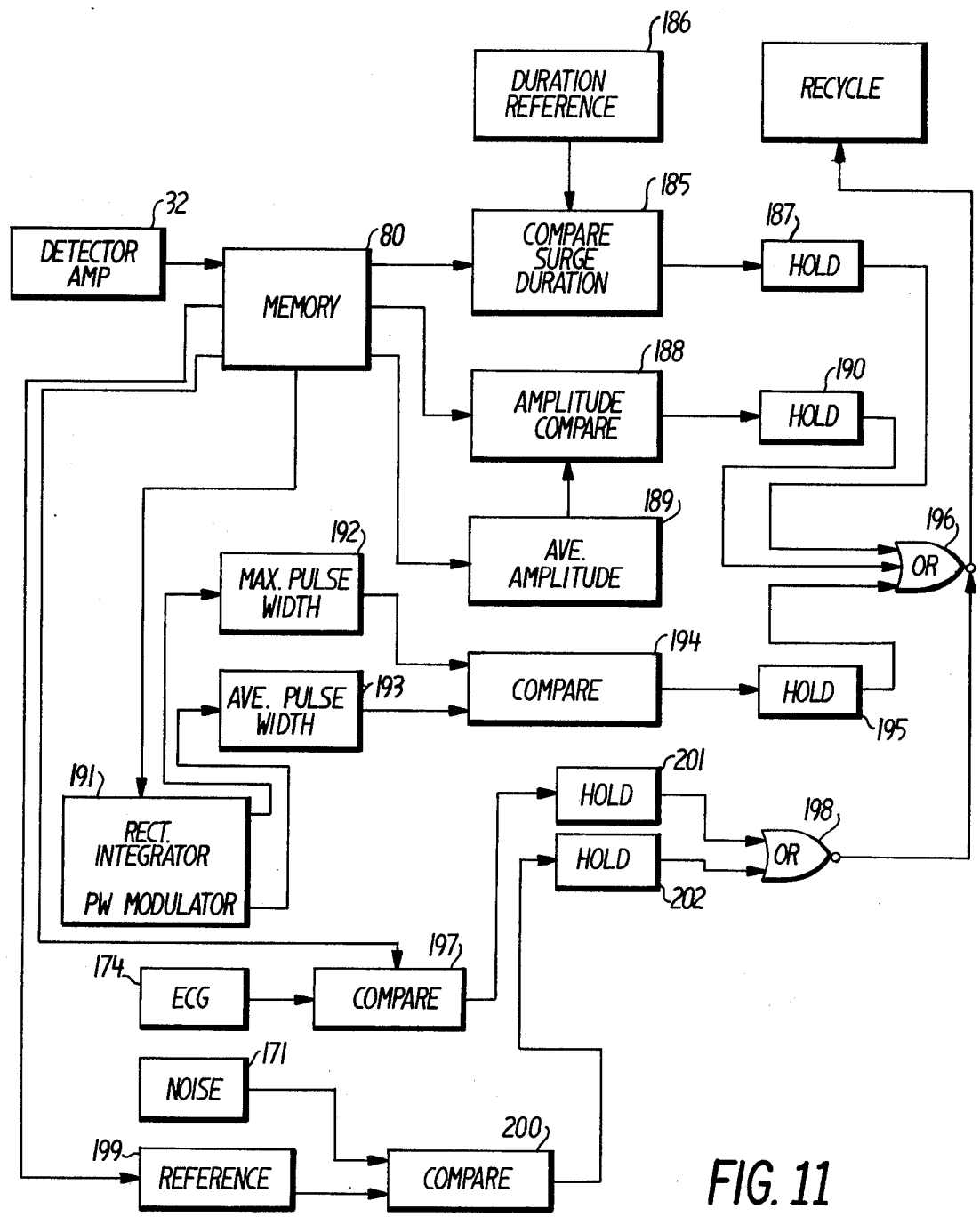
FIG. 11 is a more detailed schematic illustration showing automatic error detection in the off-line mode of operation.

FIG. 11 shown further details of a preferred system for automatically distinguishing valid signals from artifacts.

As shown, in a preferred system, three tests of the stored signals in the memory are made. In a first test, the duration of the detected surge signals are applied to a comparator 185 and compared with a reference duration 185. If the duration signals are not within a suitable reference range, there is a probability of artifact and an error is applied to a store and hold circuit 187.

In a second test, the amplitude of the burst signals from the memory 80 are applied to an amplitude comparator 188 and are there compared with the average amplitude 189 obtained from the memory. If any of the burst signals differ from the average by more than a given range, it is probable that such signal is spurious and an error is applied to sample and hold circuit 190.

In a third test, the signals from the memory 80 are amplified, rectified, and modulated in width or time by circuit 191. That pulse of maximum duration or width is selected by circuit 192 and compared at 194 with the average width obtained in circuit 193. Any deviation beyond a given range is indicative of an artifactual condition and an error is applied to store and hold circuit 195. The existance of an error on any one of the store and hold circuits 187, 190, 195 is passed through an "OR" circuit 196 to trigger the recycling of the machine in the manner as described above.

Still additional automatic testing may be provided to distinguish the existance of probable artifacts in the detected signals. Suitable electrodes and amplifiers may be provided to detect the "ECG" waves and the time phase relationship of these waves with the surge signals obtained from playback from the memory, can be obtained by phase comparator 197. An error in phase indicating a probable artifact is stored in store and hold circuit 201. Still further, a noise signal detected by a microphone 171 from other than the artery area is compared with the reference signal level 199 obtained from the memory 80 in comparator 200. Any anomaly as determined by this later comparison results in the generation of an error signal applied to a store and hold circuit 202. These later two additional error determination signals are applied to the same OR circuit as above; or to an additional OR circuit 198, and at the appropriate time in the cycle, such signals are employed to trigger a recycling of the measurement as described above, In the absence of any such eeror or probable error being determined, the memory 80 is reporduced as above described to automatically adjust the gain in the recording channel and after doing so, to play-back through the recording channel and record the measurement as described above in connection with FIG. 8.

Due to the availability and comparative inexpensiveness of integrated circuit chips providing the various logical functions and controls as descirbed above, an automatic system capable of providing an off-line automatic mode of operation may be provided without exorbitant cost and undue complexity or size.

I claim:

1. In an apparatus for automatically detecting and recording a succession of time-spaced blood flow surges occurring while a variable external pressure applied to a patient's artery is decreased over a first range including the systolic to diastolic pressure range of the patient, an inflatable cuff for applying the external pressure to the artery, normally unoperated means for pressurizing the cuff to a first predetermined value corresponding to the upper end of the first range, bleed valve means coupled to the cuff, means operative when the cuff has reached the first predetermined pressure value for depressurizing the cuff through the bleed valve means, control means including a portion of the depressurizing means and coupled to the bleed valve means and to the pressurizing means for maintaining said depressurizing at a specified constant rate throughout the first range, means for detecting successive blood flow surges caused by successive movements of the artery as the cuff is depressurized through the first range and for generating a succession of spaced first pulses corresponding to the successive detected surges, means coupled to the output of the detecting means for converting the successive first pulses into spaced, time-modulated second pulses having durations individually indicative of the time integral of the respective first pulses, a recording medium having a first axis, at least one marking means associated with and scannable along the first axis of the recording medium, each marking means including first gating means selectively operable to mark the then-adjacent portion of the recording medium along the first axis while the first gating means is operated, first means coupled to the cuff depressurizing means for scanning each marking means along the first axis of the recording medium through a region of the first axis corresponding to the first range at the constant rate maintained by the control means, and means selectively coupling successive time-modulated second pulses to the first gating means of at least a first one of the marking means for operating the last-mentioned first gating means.

2. Apparatus as defined in claim 1, in which the first pulse-generating means comprises an ultrasonic detector.

3. Apparatus as defined in claim 1, further comprising means rendered effective when the cuff has been pressurized to its first predetermined value for generating a first reference signal, and means for selectively coupling the first reference signal to the first gating means of the marking means.

4. Apparatus as defined in claim 1, further comprising means rendered effective when the cuff has been depressurized to the lower end of the first range or generating a second reference signal.

5. Apparatus as defined in claim 4, further comprising means for selectively coupling the second reference signal to the first gating means of the marking means.

6. Apparatus as defined in claim 1, further comprising means rendered effective when the cuff has been depressurized to the lower end of the first range for venting the cuff to the atmosphere.

7. Apparatus as defined in claim 1, further comprising second means for scanning the recording medium with the marking means along a second axis perpendicular to the first axis, whereby a repetitive operation of the cuff pressurizing means at spaced intervals while both the first and second scanning means are operated is effective to produce, on the recording medium, a succession of patterns of spaced marks, the successive patterns being separated by a distance along the second axis corresponding to the spaced intervals, the individual marks of each pattern having lengths corresponding to the duration of the associated time-modulated second pulses.

8. Apparatus as defined in claim 1, in which a plurality of the marking means are associated with the recording medium, and in which the apparatus further comprises means associating all of the marking means for synchronous scanning across the first axis of the recording medium.

9. Apparatus as defined in claim 8, in which at least first and second marking means are associated with the recording medium, and in which the apparatus further comprises means coupled to the output of the first pulse-generating means for generating a first electrical signal representative of the average of the amplitudes of successive first pulses over an interval long with respect to the interval between successive blood flow surges of the patient, as the cuff is depressurized, and means for selectively coupling the first electrical signal to the first gating means of the second marking means.

10. Apparatus as defined in claim 9, in which at least first, second and third marking means are associated with the recording medium, and in which the apparatus further comprises means operative in synchronism with the first pulse generating means for generating a succession of third pulses corresponding to the patient's heartbeat, and means for selectively coupling the successive third pulses to the first gating means of the third marking means.

11. Apparatus as defined in claim 10, in which first, second, third and fourth marking means are associated with the recording medium, and in which the apparatus further comprises microphone mens disposed in communicaton with the patient for generating a second electrical signal indicative of ambient noise level of the patient, and means for selectively coupling the second electrical signal to the first gating means of the fourth marking means.

12. Apparatus as defined in claim 8, in which at least first and second marking means are associated with the recording medium, and in which the apparatus further comprises means for integrating each first pulse to produce a variable-amplitude fourth pulse, amplitude quantizing means coupled to the fourth pulse producing means and having first and second outputs, the quantizing means comprising means rendered effective when the amplitude of the fourth pulse is within a first amplitude range for coupling the fourth pulse to the first output and means rendered effective when the amplitude of the fourth pulse is within a second amplitude range for coupling the fourth pulse to each of the first and second outputs, first means for translating pulses at the first output of the quantizing means to fifth pulses having durations individually proportional to the amplitudes of the pulses at the first output, second means for translating pulses at the second output of the quantizing means to sixth pulses having durations individually proportional to the amplitudes of the pulses at the second output, and means for selectively coupling the outputs of the first and second translating means to the first gating means of the first and second marking means, respectively.

13. Apparatus as defined in claim 1, in which the marking means further comprises second gating means selectively operable to mark the then-adjacent portion of the recording medium along a second axis perpendicular to the first axis while the second gating means is operated.

14. Apparatus as defined in claim 13, in which the second gating means comprises a fiber optic bundle of finite width in the direction along the second axis, whereby the width of the mark on the recording medium established by the fiber optic bundle along the second axis is indicative of the proportion of the fibers in the bundle that are simultaneously excited.

15. Apparatus as defined in claim 1, further comprising overridable timing means coupled to the cuff pressurizing means for normally repetitively operating the cuff pressurizing means.

16. Apparatus as defined in claim 15, further comprising normally disabled second gating means interposed between the output of the first pulse generating means and the input of the converting means, memory means coupled to the output of the first pulse generating means for temporarily storing the succession of first pulses, comparison means having a first input coupled to the output of the memory means and a first output energizable when the amplitude of the pulse applied to the first input from the memory means is within a first amplitude range indicative of an acceptable value, and means for coupling the first output of the comparison means to the second gating means for enabling the second gating means when the associated succession of stored first pulses are within the acceptable range.

17. Apparatus as defined in claim 16, in which the comparison means further comprises a second output energizable when the first pulse applied to its first input from the memory means is outside the acceptable range, and in which the apparatus comprises normally disabled override means coupled to the timing means for initiating operation of the cuff pressurizing means when the override means are enabled, and means coupling the second output of the comparison means to the override means for enabling the override means when the first pulse is outside the acceptable range.

18. Apparatus as defined in claim 17, further comprising alarm means, and means coupled to the override means for actuating the alarm means when the override means has been enabled by the second output of the comparison means a predetermined number of times in a selected interval.

19. Apparatus as defined in claim 16, in which the converting means comprises adjustable-gain negative feedback means for regulating the relation between the first and second pulses, and in which the apparatus further comprises means coupled to the output of the memory means for determining the signal-to-noise ratio of the first pulses stored in the memory means, and means responsive to the determining means for adjusting the gain of the feedback means in accordance with the determined value of signal-to-noise ratio.

20. Apparatus as defined in claim 16, in which the converting means comprises adjustable-gain negative feedback means for regulating the relation between the first and second pulses, and in which the apparatus further comprises means coupled to the output of the memory means for extracting the first pulse of longest duration stored in the memory means, and means responsive to the extracting means for adjusting the gain of the feedback means in accordance with the duration of the extracted first pulse.

21. Apparatus as defined in claim 20, further comprising means responsive to the adjustment means for inhibiting the operation of the cuff pressurizing means for a predetermined interval.

22. Apparatus as defined in claim 16, in which the comparison means further comprises a second input for receiving a comparison signal, and means for energizing the first output of the comparison means when the difference between the first pulses applied to the first input thereof and the comparison signal applied to the second input thereof is within the acceptable range.

23. Apparatus as defined in claim 22, further comprising means coupled to the first generating means for generating an electrical signal indicative of the average amplitude of the first pulses over an interval long with respect to the interval between successive blood flow surges of the patient, as the cuff is depressurized, and means for applying the electrical signal to the second input of the comparison means.

24. In an apparatus for automatically detecting and recording a succession of time-space blood flow surges occurring while a variable external pressure applied to a patient's artery is decreased over a first range including the systolic to diastolic pressure range of the patient, an inflatable cuff for applying the external pressure to the artery, a reference chamber having a fixed volume, normally unoperated valve means for pressurizing the reference chamber to a first preset value and for pressurizing the cuff to a second preset value corresponding to the upper end of the first range, means operative when the reference chamber has reached the first preset value of pressure for depressurizing the reference chamber at a constant rate, bleed value means coupled to the cuff, means operative when the reference chamber has reached the first preset value for depressurizing the cuff through the bleed valve means, control means including a portion of the depressurizing means and coupled to the reference chamber, the pressurized means and the bleed valve means for maintaining the depressurizing of the cuff at a linear rate porportional to the constant-rate decrease of pressure of the reference chamber throughout the first range, means for detecting successive blood flow surges caused by successive movements of the artery as the cuff is depressurized through the first range for generating a succession of spaced first pulses corresponding to the successive arterial movements, means coupled to the output of the detecting means for converting the successive first pulses into spaced, time-modulated second pulses having durations individually indicative of the time integral of the respective first pulses, a recording medium having a first axis, at least one marking means associated with the scannable along the first axis of the recording medium, each marking means including first gating means selectively operable to mark the then-adjacent portion of the medium along the first axis while the first gating means is operated, first means coupled to the cuff depressurizing means for scanning each marking means along the first axis of the recording medium at the linear rate maintained by the control means, and means selectively coupling successive time-modulated second pulses to the first gating means of at least one of the marking means for operating the first gating means.

25. Apparatus as defined in claim 24, in which the volume of the reference chamber is small relative to the volume of the cuff when the cuff is pressurized to the second preset value.

26. Apparatus as defined in claim 24, in which the control means comprises, in combination, a first pressure-regulating valve coupled to the reference chamber and to the cuff for increasing the pressure in the cuff when the pressure in the reference chamber exceeds the pressure in the cuff by more than a predetermined value, and a second pressureregulating valve coupled to the reference chamber and to the cuff for reducing the pressure in the cuff when the pressure in the reference chamber is lower than the pressure in the cuff by a predetermined value.

27. In an apparatus for automatically detecting and recording a succession of time-spaced blood flow surges occurring while a variable external pressure applied to a patient's artery is decreased over a first range including the systolic to diastolic pressure range of the patient, wherein said apparatus includes an inflatable cuff for applying the external pressure to the artery, an improved arrangement for depressurizing the cuff at a constant rate which comprises, in combination, a reference chamber having a fixed volume, means for pressurizing the reference chamber to a first preset value and for simultaneously pressurizing the cuff to a second preset value corresponding to the upper end of the first range, means operative when the reference chamber has reached the first preset value of pressure for depressurizing the reference chamber at a constant rate, bleed valve means coupled to the cuff, means operative when the reference chamber has reached the first preset value for depressurizing the cuff through the bleed valve means, and control means including a portion of the depressurizing means and coupled to the reference chamber, the pressurizing means and the bleed valve means for maintaining a predetermined difference in pressure between the reference chamber and the cuff as the reference chamber is depressurized at the constant rate.

* * * * *